(12) United States Patent
Varela (10) Patent No.: US 8,246,654 B2
(45) Date of Patent: Aug. 21, 2012

(54) TRANSFACET FIXATION ASSEMBLY AND RELATED SURGICAL METHODS

(75) Inventor: Armando Varela, Boca Raton, FL (US)

(73) Assignee: U.S. Spine, Inc., Salt Lake City, UT (US)

( * ) Notice: Subject to any disclaimer, the term of this patent is extended or adjusted under 35 U.S.C. 154(b) by 372 days.

(21) Appl. No.: 12/485,393

(22) Filed: Jun. 16, 2009

(65) Prior Publication Data

US 2009/0312798 A1    Dec. 17, 2009

Related U.S. Application Data

(60) Provisional application No. 61/061,694, filed on Jun. 16, 2008.

(51) Int. Cl.
*A61B 17/70* (2006.01)
(52) U.S. Cl. ........................................................ 606/247
(58) Field of Classification Search .............. 606/86 A, 606/60, 246–279, 64, 300–321, 61, 219; 470/19; 403/346, 22, 46, 52, 56, 348, DIG. 12
See application file for complete search history.

(56) References Cited

U.S. PATENT DOCUMENTS

| 3,124,971 | A | * | 3/1964 | Peters et al. ................ 74/579 R |
|---|---|---|---|---|
| 4,359,794 | A | * | 11/1982 | Bouwman ..................... 470/197 |
| 5,246,303 | A | * | 9/1993 | Trilla et al. .................... 403/353 |
| 5,643,264 | A | * | 7/1997 | Sherman et al. .............. 606/275 |
| 7,799,057 | B2 | * | 9/2010 | Hudgins et al. ............... 606/247 |
| 2003/0040746 | A1 | * | 2/2003 | Mitchell et al. ................ 606/61 |
| 2003/0220643 | A1 | * | 11/2003 | Ferree ............................ 606/61 |
| 2004/0116927 | A1 | * | 6/2004 | Graf ............................... 606/61 |
| 2004/0172024 | A1 | * | 9/2004 | Gorek ............................ 606/61 |
| 2005/0038432 | A1 | * | 2/2005 | Shaolian et al. ............... 606/61 |
| 2007/0055236 | A1 | * | 3/2007 | Hudgins et al. ................ 606/61 |
| 2008/0058812 | A1 | * | 3/2008 | Zehnder ......................... 606/61 |
| 2008/0255618 | A1 | * | 10/2008 | Fisher et al. ................. 606/247 |
| 2008/0255622 | A1 | * | 10/2008 | Mickiewicz et al. ......... 606/319 |
| 2009/0187219 | A1 | * | 7/2009 | Pachtman et al. ............ 606/324 |

* cited by examiner

*Primary Examiner* — Eduardo C Robert
*Assistant Examiner* — James Palmer
(74) *Attorney, Agent, or Firm* — Philips Ryther & Winchester; Matthew D. Thayne (57) ABSTRACT

The present invention provides a transfacet fixation assembly, including: an engaging bolt; and a receiving bolt selectively coupled to and engaged with the engaging bolt at an angle of between about 30 degrees and about 120 degrees; wherein each of the engaging bolt and the receiving bolt is configured to be disposed through a hole or bore formed through one of a plurality of bony structures making up a portion of a facet joint of a spine. Optionally, the engaging bolt includes a spherical distal end for engaging a locking sleeve disposed at a distal end of the receiving bolt.

23 Claims, 9 Drawing Sheets

TRANSFACET FIXATION ASSEMBLY AND RELATED SURGICAL METHODS

CROSS-REFERENCE TO RELATED APPLICATION

The present non-provisional patent application claims the benefit of priority of U.S. Provisional Patent Application No. 61/061,694, filed on Jun. 16, 2008, and entitled "TRANSFACET FIXATION ASSEMBLY AND RELATED SURGICAL METHODS," the contents of which are incorporated in full by reference herein.

FIELD OF THE INVENTION

The present invention relates generally to minimally invasive, surgically implantable spinal devices and systems. More specifically, the present invention relates to a transfacet fixation assembly that is used to immobilize a facet joint of the spine and related surgical methods. This transfacet fixation assembly is robust and flexible, such that it can be used with a variety of spinal morphologies.

BACKGROUND OF THE INVENTION

In the treatment of various spinal injuries, diseases, and degenerative conditions, it is desirable to immobilize a facet joint of the spine (e.g. in support of a spinal fusion) by means other than conventional pedicle screw systems or the like. A variety of minimally invasive, surgically implantable devices and systems have been developed in order to serve such purposes. Typically, these devices and systems utilize a single transfacet bolt or the like that is disposed through the facet joint. Other clamping mechanisms have also been developed. However, not all spinal morphologies support the utilization of such transfacet bolts or clamping mechanisms. In such cases, the use of a substantially V-shaped transfacet bolt assembly or the like is desirable. However, no such substantially V-shaped transfacet bolt assembly is currently available or in existence.

BRIEF SUMMARY OF THE INVENTION

In various exemplary embodiments, the present invention provides a substantially V-shaped transfacet bolt assembly or the like for immobilizing a facet joint of the spine. This substantially V-shaped transfacet bolt assembly or the like is robust and flexible, such that it can be used with a variety of spinal morphologies.

In one exemplary embodiment, the present invention provides a transfacet fixation assembly, including: an engaging bolt; and a receiving bolt selectively coupled to and engaged with the engaging bolt at an angle of between about 30 degrees and about 120 degrees; wherein each of the engaging bolt and the receiving bolt is configured to be disposed through a hole or bore formed through one of a plurality of bony structures making up a portion of a facet joint of a spine. Optionally, the engaging bolt includes a spherical distal end for engaging a locking sleeve disposed at a distal end of the receiving bolt. Optionally, the locking sleeve includes a slot mechanism that locks the engaging bolt to the receiving bolt. Preferably, each of the engaging bolt and the receiving bolt is configured to selectively receive a washer. Optionally, each of the washers includes a superior surface including a radial, ratcheting antirotation surface disposed concentrically about a central hole or bore of the washer. Optionally, each of the washers includes an inferior surface including a radial antirotation friction structure disposed concentrically about a central hole or bore of the washer. Preferably, the radial antirotation friction structures are configured to engage the bony structures of the facet joint of the spine when the washers are in place. Optionally, each of the engaging bolt and the receiving bolt is configured to selectively receive a nut. Optionally, each of the nuts includes an inferior surface including a radial, ratcheting antirotation surface disposed concentrically about a central hole or bore of the nut. Preferably, the radial, ratcheting antirotation surfaces of the nuts are configured and positioned to engage radial, ratcheting antirotation surfaces of washers, thereby preventing the backing off of the nuts once installed.

In another exemplary embodiment, the present invention provides a transfacet fixation method, including: providing an engaging bolt; and providing a receiving bolt selectively coupled to and engaged with the engaging bolt at an angle of between about 30 degrees and about 120 degrees; wherein each of the engaging bolt and the receiving bolt is configured to be disposed through a hole or bore formed through one of a plurality of bony structures making up a portion of a facet joint of a spine. Optionally, the engaging bolt includes a spherical distal end for engaging a locking sleeve disposed at a distal end of the receiving bolt. Optionally, the locking sleeve includes a slot mechanism that locks the engaging bolt to the receiving bolt. Preferably, each of the engaging bolt and the receiving bolt is configured to selectively receive a washer. Optionally, each of the washers includes a superior surface including a radial, ratcheting antirotation surface disposed concentrically about a central hole or bore of the washer. Optionally, each of the washers includes an inferior surface including a radial antirotation friction structure disposed concentrically about a central hole or bore of the washer. Preferably, the radial antirotation friction structures are configured to engage the bony structures of the facet joint of the spine when the washers are in place. Optionally, each of the engaging bolt and the receiving bolt is configured to selectively receive a nut. Optionally, each of the nuts includes an inferior surface including a radial, ratcheting antirotation surface disposed concentrically about a central hole or bore of the nut. Preferably, the radial, ratcheting antirotation surfaces of the nuts are configured and positioned to engage radial, ratcheting antirotation surfaces of washers, thereby preventing the backing off of the nuts once installed.

BRIEF DESCRIPTION OF THE DRAWINGS

The present invention is illustrated and described herein with reference to the various drawings, in which like reference numbers are used to denote like assembly components/method steps, as appropriate, and in which.

DETAILED DESCRIPTION OF THE INVENTION

Figure 1:
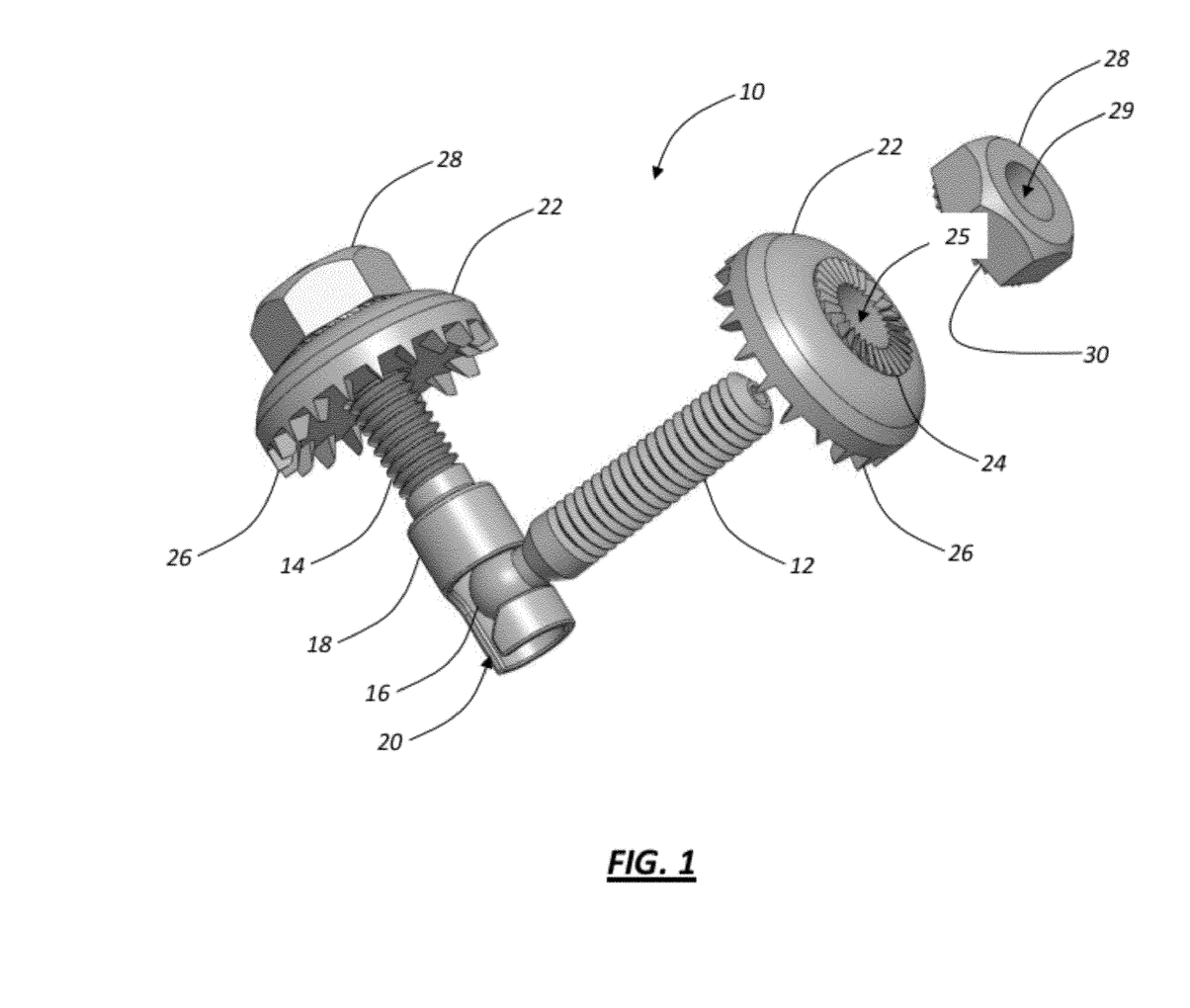
FIG. 1 is a partially exploded perspective view of one embodiment of the transfacet fixation assembly of the present invention.

Referring now to FIG. 1, in one exemplary embodiment, the transfacet fixation assembly 10 of the present invention includes a cannulated engaging bolt 12 that is selectively coupled to and engaged with a cannulated receiving bolt 14 at an angle of between about 30 degrees and about 120 degrees, although other angles may of course be utilized. Each of the cannulated engaging bolt 12 and cannulated receiving bolt 14 is threaded and is configured to be disposed through a threaded or non-threaded hole or bore drilled through one of the bony structures making up a portion of the facet joint of a spine. It will be readily apparent to those of ordinary skill in the art that other anatomical joints may also be joined using the transfacet fixation assembly 10 of the present invention.

Figure 2:
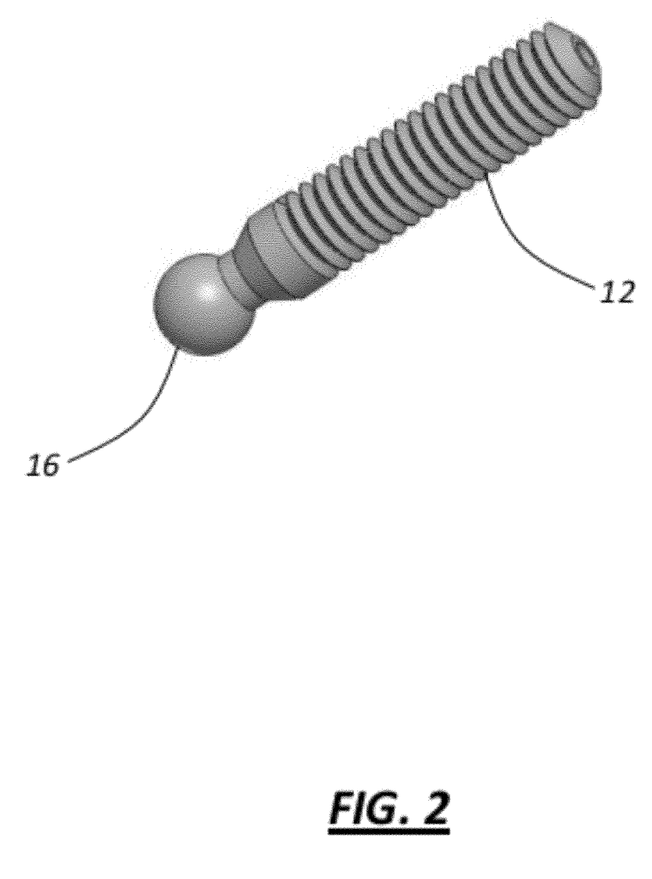
FIG. 2 is a perspective view of one exemplary embodiment of the cannulated engaging bolt of FIG. 1.
Figure 3:
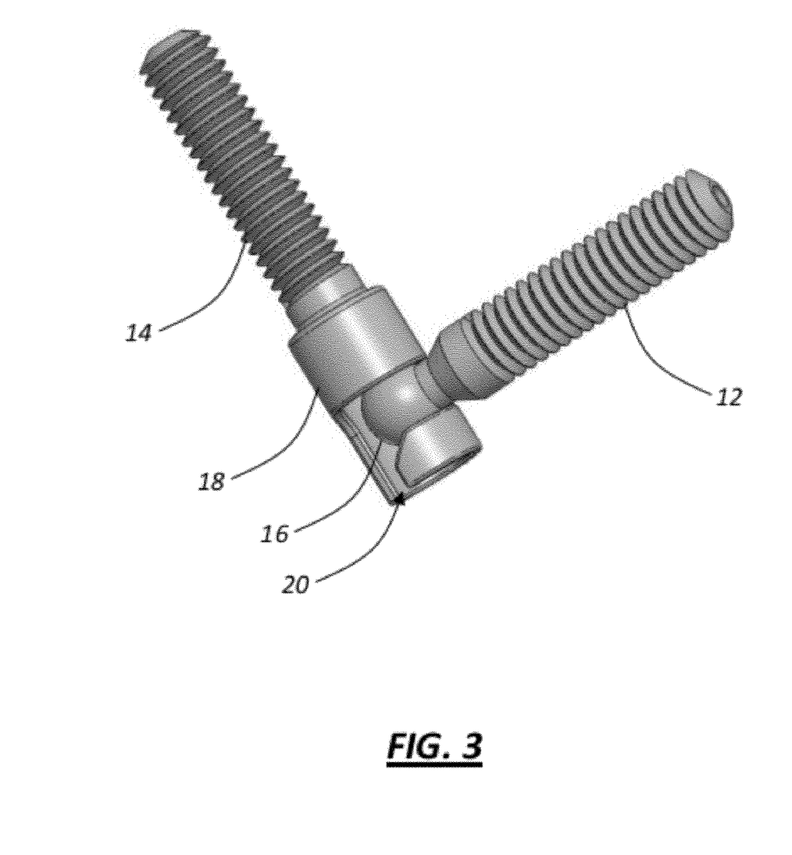
FIG. 3 is a perspective view of the cannulated engaging bolt of FIGS. 1 and 2 engaging one exemplary embodiment of the cannulated receiving bolt of FIG. 1.
Figure 4:
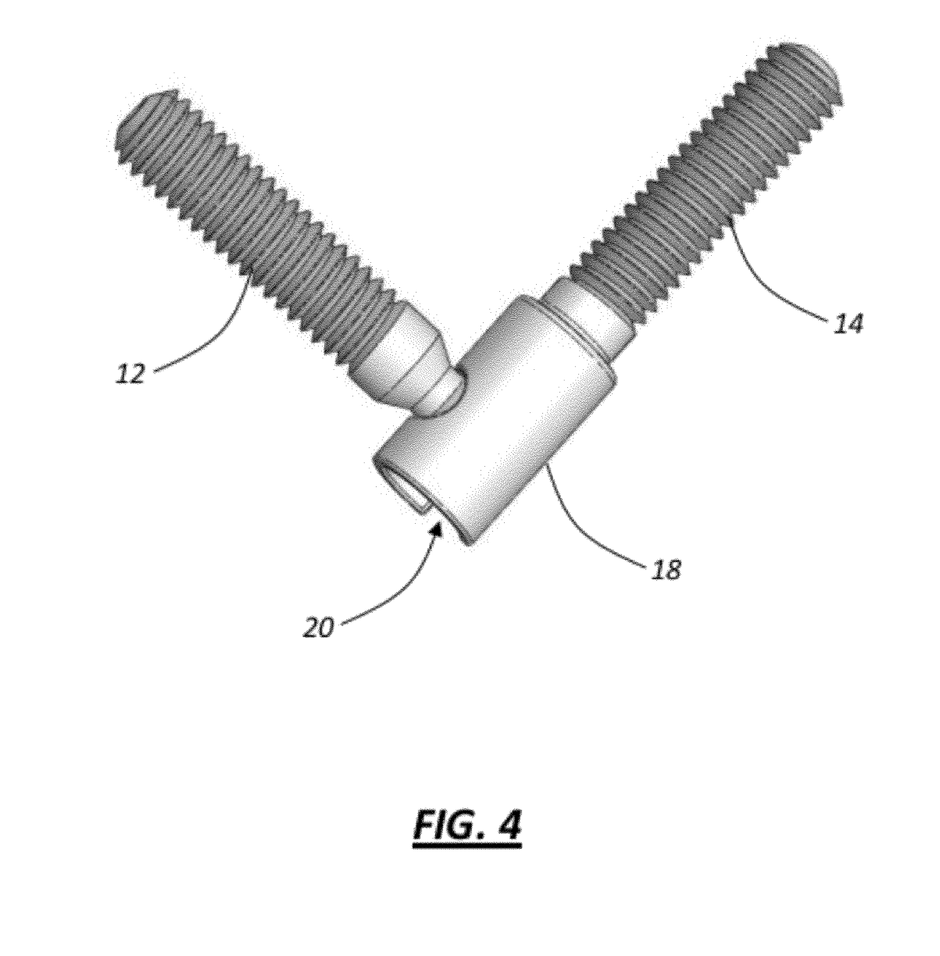
FIG. 4 is another perspective view of the cannulated engaging bolt of FIGS. 1-3 engaging the cannulated receiving bolt of FIGS. 1 and 3.

Referring now to FIGS. 2-4, in one exemplary embodiment, the cannulated engaging bolt 12 has a spherical distal end 16 (FIGS. 2 and 3) for engaging a locking sleeve 18 (FIGS. 3 and 4) disposed at the distal end of the cannulated receiving bolt 14 (FIGS. 3 and 4). As illustrated, this locking sleeve 18 includes a slot mechanism 20 (FIGS. 3 and 4) that locks the cannulated engaging bolt 12 to the cannulated receiving bolt 14 with a half turn, for example, while optionally allowing some relative movement between the cannulated engaging bolt 12 and the cannulated receiving bolt 14 along one or more predetermined axes. However, it will be readily apparent to those of ordinary skill in the art that other suitable locking mechanisms may be used, provided that the distal ends of the cannulated engaging bolt 12 and the cannulated receiving bolt 14 are joined, holding the cannulated engaging bolt 12 and the cannulated receiving bolt 14 at a predetermined angle relative to one another.

Figure 5:
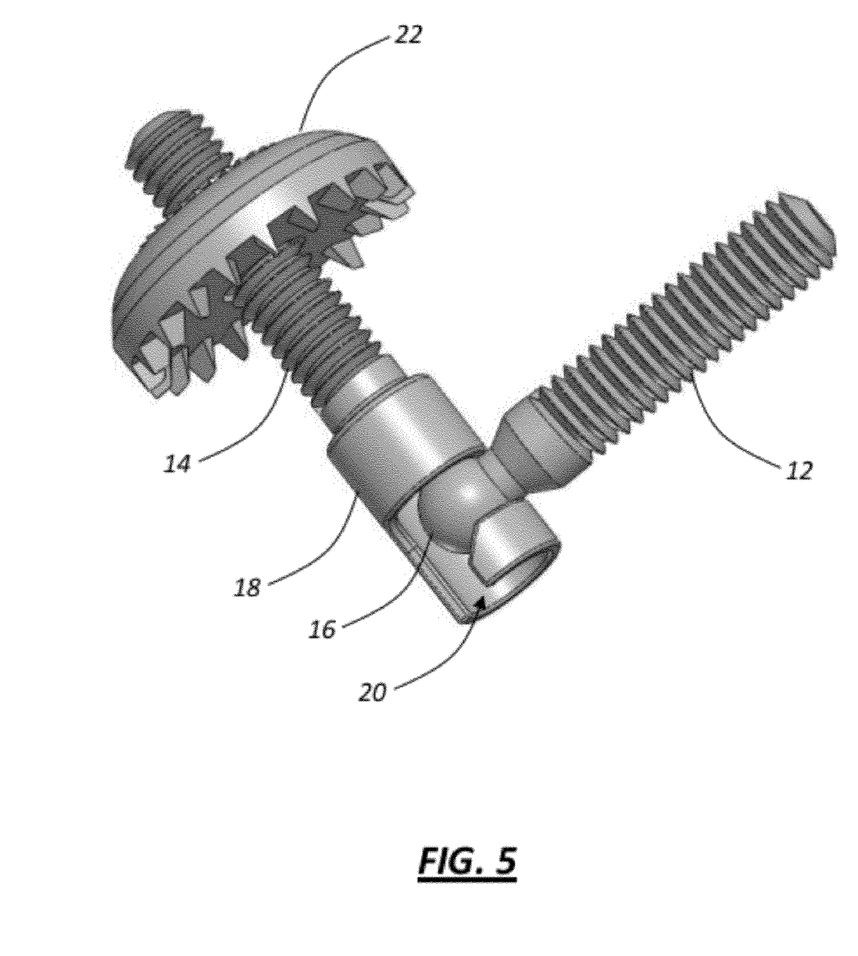
FIG. 5 is a perspective view of one exemplary embodiment of the cannulated receiving bolt washer of FIG. 1 engaging the cannulated receiving bolt of FIGS. 1, 3, and 4.
Figure 6:
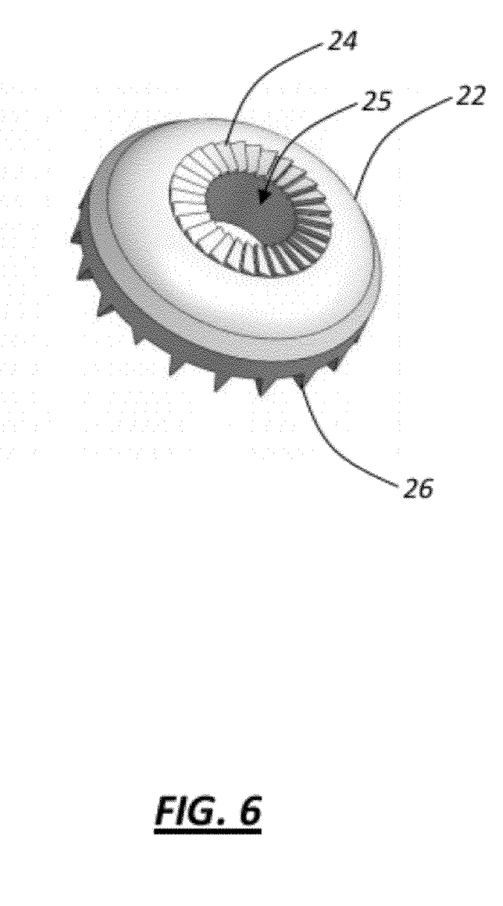
FIG. 6 is a perspective view of the cannulated receiving/engaging bolt washer of FIGS. 1 and 5.
Figure 7:
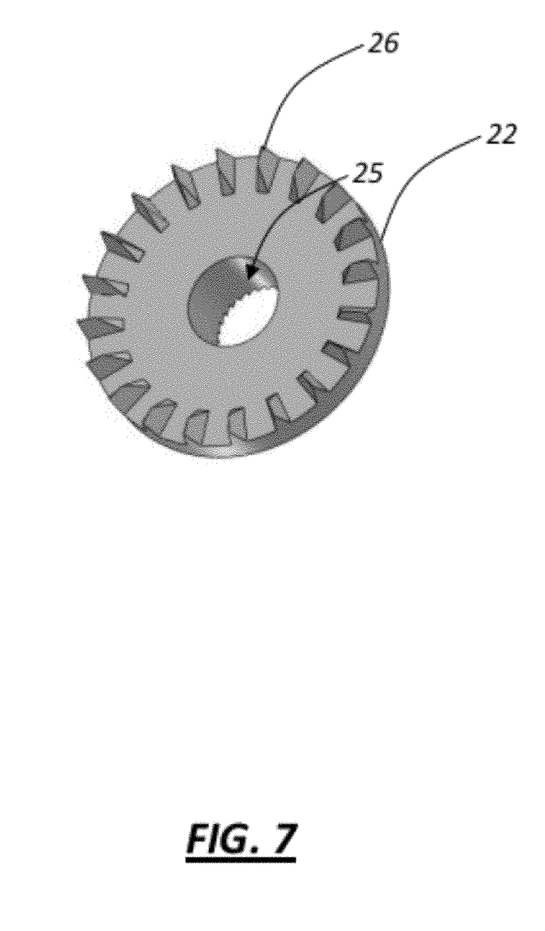
FIG. 7 is another perspective view of the cannulated receiving/engaging bolt washer of FIGS. 1, 5, and 6.

Referring now to FIGS. 1 and 5, in use, each of the cannulated engaging bolt 12 and cannulated receiving bolt 14 selectively receive a threaded or non-threaded washer 22. As illustrated in FIGS. 6 and 7, in one exemplary embodiment, the superior surfaces of these washers 22 each include a radial, ratcheting antirotation surface 24 (FIG. 6) disposed concentrically about the central hole or bore 25 of the washer 22. This radial, ratcheting antirotation surface 24 may consist of a plurality of raised detents or the like. The inferior surfaces of these washers 22 each include a radial set of gripping teeth 26 or other friction structures disposed concentrically about the central hole or bore 25 of the washer 22. These gripping teeth 26 or other friction structures are designed to engage the bony structures of the facet joint of the spine when the washers 22 are in place, thereby securely mating the transfacet fixation assembly 10 (FIG. 1) of the present invention with the bony structures and preventing relative movement and/or rotation.

Figure 8:
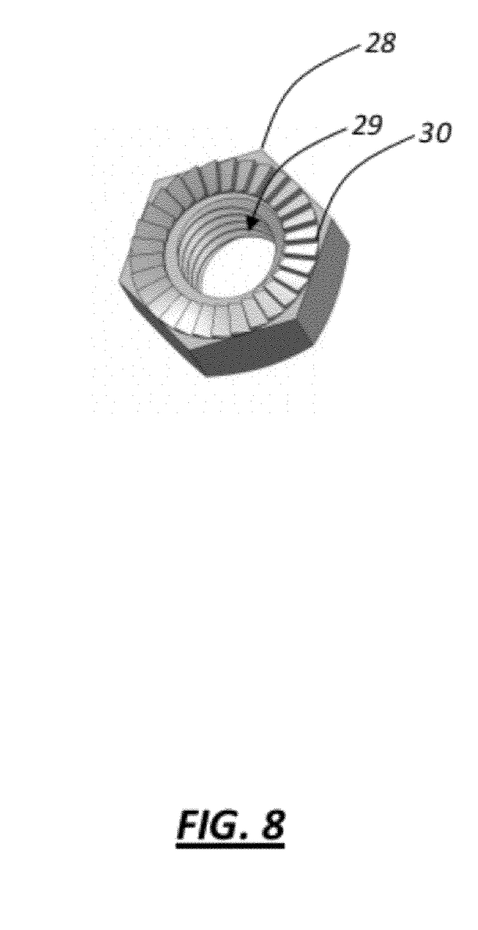
FIG. 8 is a perspective view of one exemplary embodiment of the cannulated receiving/engaging bolt nut of FIG. 1.
Figure 9:
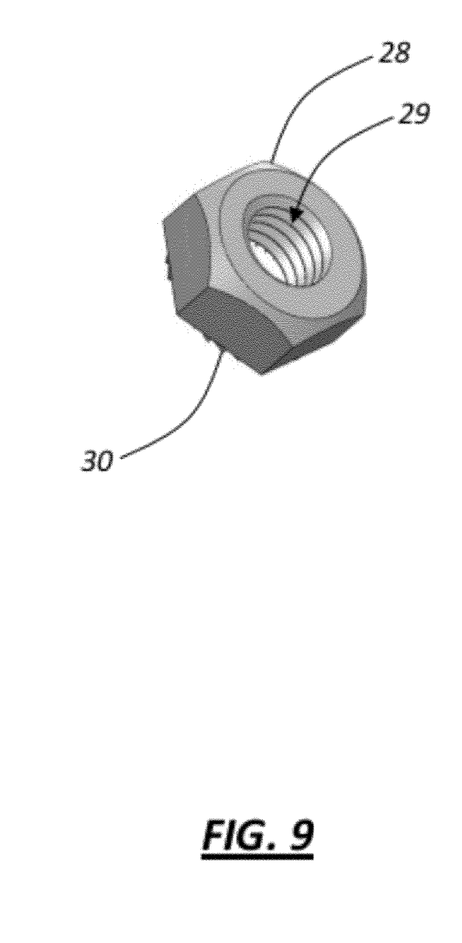
FIG. 9 is another perspective view of the cannulated receiving/engaging bolt nut of FIGS. 1 and 8.

Referring again to FIG. 1, in use, each of the cannulated engaging bolt 12 and cannulated receiving bolt 14 selectively receive a threaded nut 28 or other retention/locking mechanism. As illustrated in FIGS. 8 and 9, in one exemplary embodiment, the inferior surfaces of these nuts 28 each include a radial, ratcheting antirotation surface 30 disposed concentrically about the central hole or bore 29 of the nut 28. Again, this radial, ratcheting antirotation surface 30 may consist of a plurality of raised detents or the like. The radial, ratcheting antirotation surfaces 30 of the nuts 28 are configured and positioned to engage the radial, ratcheting antirotation surfaces 24 of the washers 22, thereby preventing the backing off of the nuts 28 once installed. The nuts may also each include a polymeric material or the like disposed within their central hole or bore 29 for preventing backing off.

Preferably, the transfacet fixation assembly 10 (FIG. 1) of the present invention is sized such that it fits a variety of spinal or other anatomical morphologies and its components are manufactured from surgically-implantable material(s), well known to those of ordinary skill in the art. It will be readily apparent to those of ordinary skill in the art that various means may be used to fasten the "arms" of the transfacet fixation assembly 10 to various bony structures, provided the V-configuration is maintained.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A transfacet fixation assembly, comprising:
an engaging bolt;
a receiving bolt configured to be selectively coupled to and engaged with the engaging bolt;
a locking sleeve comprising a slot mechanism configured to lock the engaging bolt with the receiving bolt by a partial rotation of the engaging bolt with respect to the receiving bolt,
wherein each of the engaging bolt and the receiving bolt is configured to be disposed through a hole or bore formed through one of a plurality of bony structures making up a portion of a facet joint of a spine;
an engaging bolt washer; and
a receiving bolt washer, wherein the engaging bolt is configured to selectively receive the engaging bolt washer and the receiving bolt is configured to selectively receive the receiving bolt washer.

2. The transfacet fixation assembly of claim 1, wherein the locking sleeve is disposed at a distal end of the receiving bolt, and wherein the engaging bolt comprises a spherical distal end for engaging the locking sleeve.

3. The transfacet fixation assembly of claim 1, wherein each of the washers comprises a superior surface comprising a radial, ratcheting antirotation surface disposed concentrically about a central hole or bore of the washer.

4. The transfacet fixation assembly of claim 1, wherein each of the washers comprises an inferior surface comprising a radial antirotation friction structure disposed concentrically about a central hole or bore of the washer.

5. The transfacet fixation assembly of claim 4, wherein the radial antirotation friction structures are configured to engage the bony structures of the facet joint of the spine when the washers are in place.

6. The transfacet fixation assembly of claim 1, further comprising an engaging bolt nut and a receiving bolt nut, wherein the engaging bolt is configured to selectively receive the engaging bolt nut and the receiving bolt is configured to selectively receive the receiving bolt nut.

7. The transfacet fixation assembly of claim 6, wherein each of the nuts comprise an inferior surface comprising a radial, ratcheting antirotation surface disposed concentrically about a central hole or bore of the nut.

8. The transfacet fixation assembly of claim 7, wherein the radial, ratcheting antirotation surfaces of the nuts are configured and positioned to engage radial, ratcheting antirotation surfaces of washers, thereby preventing the backing off of the nuts once installed.

9. The transfacet fixation assembly of claim 1, wherein the receiving bolt is configured to be selectively coupled to and engaged with the engaging bolt at an angle of between about 30 degrees and about 120 degrees.

10. A transfacet fixation method, comprising:
forming a first hole or bore through one of a plurality of bony structures making up a portion of a facet joint of a spine;
forming a second hole or bore through one of a plurality of bony structures making up a portion of a facet joint of the spine;
inserting an engaging bolt through the first hole or bore;
inserting a receiving bolt through the second hole or bore;
coupling the engaging bolt with the receiving bolt via a locking sleeve comprising a slot mechanism; and
locking the engaging bolt with the receiving bolt by a partial rotation of the engaging bolt with respect to the receiving bolt.

11. The transfacet fixation method of claim 10, wherein the locking sleeve is disposed at a distal end of the receiving bolt, and wherein the engaging bolt comprises a spherical distal end for engaging the locking sleeve.

12. The transfacet fixation method of claim 10, further comprising selectively engaging each of the engaging bolt and the receiving bolt with a washer.

13. The transfacet fixation method of claim 12, wherein each of the washers comprises a superior surface comprising a radial, ratcheting antirotation surface disposed concentrically about a central hole or bore of the washer.

14. The transfacet fixation method of claim 12, wherein each of the washers comprises an inferior surface comprising a radial antirotation friction structure disposed concentrically about a central hole or bore of the washer.

15. The transfacet fixation method of claim 14, wherein the radial antirotation friction structures are configured to engage the bony structures of the facet joint of the spine when the washers are in place.

16. The transfacet fixation method of claim 10, wherein each of the engaging bolt and the receiving bolt is configured to selectively receive a nut.

17. The transfacet fixation method of claim 16, wherein each of the nuts comprises an inferior surface comprising a radial, ratcheting antirotation surface disposed concentrically about a central hole or bore of the nut.

18. The transfacet fixation method of claim 17, wherein the radial, ratcheting antirotation surfaces of the nuts are configured and positioned to engage radial, ratcheting antirotation surfaces of washers, thereby preventing the backing off of the nuts once installed.

19. The method of claim 10, wherein the receiving bolt is coupled to the engaging bolt at an angle of between about 30 degrees and about 120 degrees.

20. A transfacet fixation assembly, comprising:
an engaging bolt;
a receiving bolt configured to be selectively coupled to and engaged with the engaging bolt;
a locking sleeve comprising a slot mechanism configured to lock the engaging bolt with the receiving bolt by a partial rotation of the engaging bolt with respect to the receiving bolt,
wherein each of the engaging bolt and the receiving bolt is configured to be disposed through a hole or bore formed through one of a plurality of bony structures making up a portion of a facet joint of a spine;
an engaging bolt nut; and
a receiving bolt nut, wherein the engaging bolt is configured to selectively receive the engaging bolt nut and the receiving bolt is configured to selectively receive the receiving bolt nut.

21. The transfacet fixation assembly of claim 20, wherein the locking sleeve is disposed at a distal end of the receiving bolt, and wherein the engaging bolt comprises a spherical distal end for engaging the locking sleeve.

22. The transfacet fixation assembly of claim 20, wherein each of the nuts comprise an inferior surface comprising a radial, ratcheting antirotation surface disposed concentrically about a central hole or bore of the nut.

23. The transfacet fixation assembly of claim 22, wherein the radial, ratcheting antirotation surfaces of the nuts are configured and positioned to engage radial, ratcheting antirotation surfaces of washers, thereby preventing the backing off of the nuts once installed.

* * * * *